United States Patent [19]

Parg et al.

[11] Patent Number: 4,576,630
[45] Date of Patent: Mar. 18, 1986

[54] SUBSTITUTED 4,5-DIMETHOXYPYRIDAZONES, HERBICIDES CONTAINING THESE COMPOUNDS, AND THEIR USE FOR CONTROLLING UNDESIRABLE PLANT GROWTH

[75] Inventors: Adolf Parg, Bad Durkheim; Gerhard Hamprecht, Weinheim; Hubert Sauter, Mannheim; Bruno Wuerzer, Otterstadt, all of Fed. Rep. of Germany

[73] Assignee: BASF Aktiengesellschaft, Fed. Rep. of Germany

[21] Appl. No.: 617,929

[22] Filed: Jun. 6, 1984

[30] Foreign Application Priority Data

Jun. 10, 1983 [DE] Fed. Rep. of Germany ....... 3321007

[51] Int. Cl.$^4$ ............ A01N 43/58; C07D 237/16
[52] U.S. Cl. ......................................... 71/92; 544/240
[58] Field of Search ............................. 544/240; 71/92

[56] References Cited

U.S. PATENT DOCUMENTS

| 3,326,660 | 6/1967 | Reicheneder et al. | 71/2.5 |
| 3,697,522 | 10/1972 | Reicheneder et al. | 260/250 A |
| 4,360,672 | 11/1982 | Parg et al. | 544/240 |
| 4,523,946 | 6/1985 | Parg et al. | 544/240 |

FOREIGN PATENT DOCUMENTS

| 0037925 | 10/1981 | European Pat. Off. | 544/240 |
| 3123715 | 12/1982 | Fed. Rep. of Germany | 544/240 |
| 3202678 | 8/1983 | Fed. Rep. of Germany | 544/240 |

Primary Examiner—Donald G. Daus
Assistant Examiner—Mary E. Ceperley
Attorney, Agent, or Firm—Keil & Weinkauf

[57] ABSTRACT 4,5-Dimethoxypyridazones of the formula

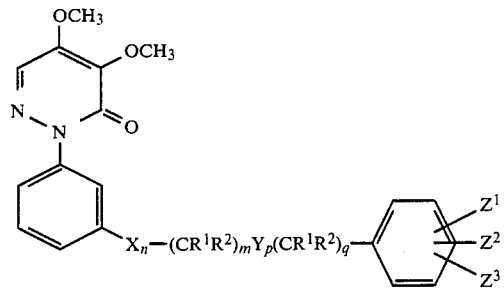

where X and Y are each oxygen, sulfur, a sulfinyl group or a sulfo group, $R^1$ and $R^2$ and each hydrogen or alkyl, $Z^1$, $Z^2$ and $Z^3$ are each hydrogen, halogen, nitro, cyano, alkyl, haloalkyl, alkoxy, haloalkoxy, alkylmercapto, haloalkylmercapto, alkylsulfinyl or alkylsulfonyl, n and p are each 0 or 1 and m and q are each 0 to 8, are used for controlling undesirable plant growth.

15 Claims, No Drawings

SUBSTITUTED 4,5-DIMETHOXYPYRIDAZONES, HERBICIDES CONTAINING THESE COMPOUNDS, AND THEIR USE FOR CONTROLLING UNDESIRABLE PLANT GROWTH

The present invention relates to substituted 4,5-dimethoxypyridazones, herbicides which contain these pyridazones as active ingredients, and methods of controlling undesirable plant growth with these active ingredients or herbicides.

It is known that 1-phenyl-4,5-dimethoxypyridaz-6-one has a broad herbicidal action and can be used as a total herbicide (U.S. Pat. No. 3,326,660). The active ingredient can cause damage to plants both when applied before planting the plants and when the leaves are treated. 4,5-Disubstituted 1-(m-trifluoromethylphenyl)-pyridaz-6-ones and 4,5-disubstituted 1-phenoxyphenyl-pyridaz-6-ones having similar herbicidal properties are also known (U.S. Pat. Nos. 3,697,522 and 4,360,672).

We have found that substituted 4,5-dimethoxypyridazones of the formula

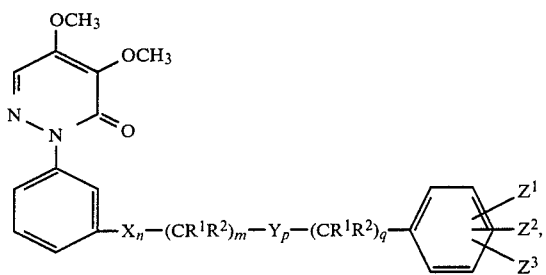

(I)

where X and Y independently of one another are each oxygen, sulfur, a sulfinyl group or a sulfo group, $R^1$ and $R^2$ independently of one another are each hydrogen or $C_1$–$C_4$-alkyl, $Z^1$, $Z^2$ and $Z^3$ independently of one another are each hydrogen, halogen, nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylmercapto, $C_1$–$C_4$-haloalkylmercapto, $C_1$–$C_4$-alkylsulfinyl or $C_1$–$C_4$-alkylsulfonyl, n and p are each 0 or 1 and m and q are each 0 to 8, possess good herbicidal activity and surprisingly are tolerated by crops or have a selective herbicidal action when used in crops.

In formula I, $R^1$ and $R^2$ independently of one another can each be hydrogen or $C_1$–$C_4$-alkyl, such as methyl, ethyl, n-propyl, i-propyl, n-butyl or tert.-butyl, and $Z^1$, $Z^2$ and $Z^3$ independently of one another can each be, for example, hydrogen, halogen, such as fluorine, chlorine or bromine, nitro, cyano, $C_1$–$C_4$-alkyl, such as methyl, ethyl, n-propyl, i-propyl, n-butyl or tert.-butyl, $C_1$–$C_4$-haloalkyl, such as trifluoromethyl, difluoromethyl, fluoromethyl, trichloromethyl, dichloromethyl, chloromethyl, difluorochloromethyl, 1-chloroethyl, 2-chloroethyl, 1-fluoroethyl, 2-fluoroethyl, 2,2,2-trichloroethyl, 2,2,2-trifluoroethyl, 1,1,2,2-tetrafluoroethyl, 1,1,2-trifluoro-2-chloroethyl or 1,1,2,2,2-pentafluoroethyl, $C_1$–$C_4$-alkoxy, such as methoxy, ethoxy, n-propoxy, i-propoxy or tert.-butoxy, $C_1$–$C_4$-haloalkoxy, such as trichloromethoxy, trifluoromethoxy, 1-chloroethoxy, 2-chloroethoxy, 1-fluoroethoxy, 2-fluoroethoxy, 2,2,2-trichloroethoxy, 2,2,2-trifluoroethoxy, 1,1,2,2-tetrafluoroethoxy or 1,1,2,2,2-pentafluoroethoxy, $C_1$–$C_4$-alkylmercapto, such as methylmercapto or ethylmercapto, $C_1$–$C_4$-haloalkylmercapto, such as trichloromethylmercapto or trifluoromethylmercapto, $C_1$–$C_4$-alkylsulfinyl, such as methylsulfinyl or ethylsulfinyl, or $C_1$–$C_4$-alkylsulfonyl, such as methylsulfonyl or ethylsulfonyl.

Preferred compounds of the formula I are those in which X and Y independently of one another are each oxygen or sulfur, $R^1$ and $R^2$ independently of one another are each hydrogen or $C_1$–$C_4$-alkyl, $Z^1$, $Z^2$ and $Z^3$ independently of one another are each hydrogen, halogen, $C_1$–$C_4$-alkyl, $C_1$–$C_4$-haloalkyl, $C_1$–$C_4$-alkoxy or $C_1$–$C_4$-haloalkoxy, n and p are each 0 or 1 and m and q are each 0 to 8.

Other preferred compounds of the formula I are those in which $R^1$ and $R^2$ are each hydrogen, $Z^1$ is hydrogen, $Z^2$ and $Z^3$ are each halogen, n is 0, m and p are each 1 and q is 0.

The 4,5-dimethoxypyridazones of the formula I are obtained by reacting a 4,5-dihalopyridazone of the formula

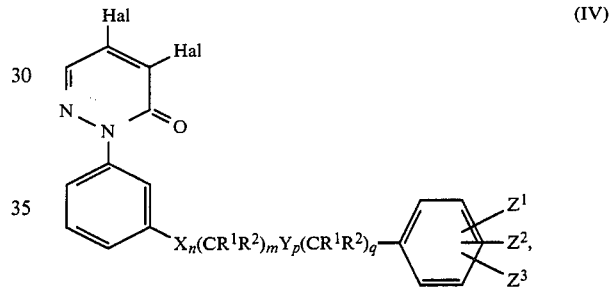

(IV)

where X, Y, $R^1$, $R^2$, $Z^1$, $Z^2$, $Z^3$, n, m, p and q have the above meanings and Hal is halogen, in particular chlorine or bromine, with about the stoichiometric amount of an alkali metal methylate in the presence of an inert organic solvent at in general no higher than 100° C., under atmospheric or superatmospheric pressure (from 1 to 10 bar), continuously or batchwise (process a).

If 1-[3'-(4"-chlorobenzyloxy)-phenyl]-4,5-dichloropyridaz-6-one and sodium methylate are used as starting materials, the course of the reaction can be represented by the following equation:

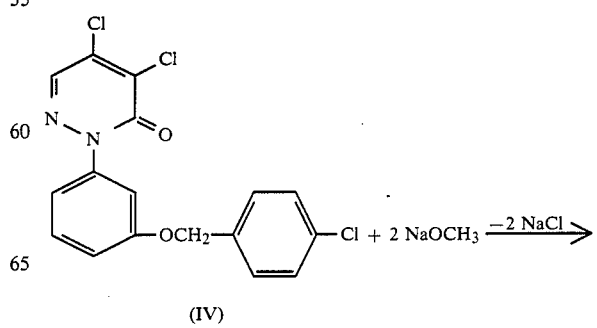

(IV)

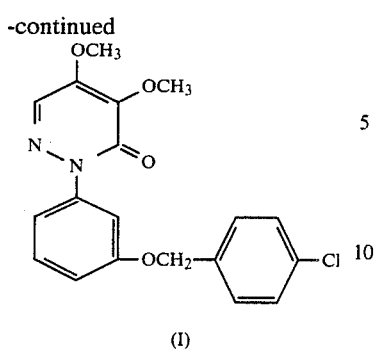

(I)

Advantageously, the dihalopyridazone IV is first dissolved or suspended in an organic solvent, eg. toluene, and then reacted with the appropriate amount of the alcoholate. The reaction takes place under atmospheric or superatmospheric pressure, in general in the course of 12 hours at no higher than 100° C., preferably from 40° to 80° C., and can be carried out batchwise or continuously. The reaction mixture can be worked up in a conventional manner. If the end product is obtained in solid form, it is isolated by, for example, filtering off the precipitate under suction. If, on the other hand, the end product remains dissolved in the solvent, the latter is distilled off under reduced pressure, the residue is stirred with water, and the product is filtered off under suction. The product can be purified by, for example, recrystallization or chromatography.

Dihalopyridazones of the formula IV can be obtained, for example, by reacting a phenylhydrazine of the formula V $$\text{NHNH}_2\text{—}X_n(CR^1R^2)_mY_p(CR^1R^2)_q\text{—}\begin{array}{c}Z^1\\Z^2\\Z^3\end{array} \quad (V)$$

where X, Y, $R^1$, $R^2$, $Z^1$, $Z^2$, $Z^3$, n, m, p and q have the above meanings, with a 3-formyl-2,3-dihaloacrylic acid of the formula $$\text{HO}_2\text{C—C}=\text{C—CHO} \quad (VI)$$
$$\phantom{\text{HO}_2\text{C—}}|\phantom{=}|$$
$$\phantom{\text{HO}_2\text{C—C}=}\text{Hal Hal}$$

where Hal is chlorine or bromine, and subjecting the resulting dihaloacrylic acid semicarbazone to a cyclization reaction.

The conversion to the corresponding dihaloacrylic acid semicarbazone is carried out at room temperature, for example in an aqueous solution containing a mineral acid or in a water-containing or anhydrous organic solvent, such as ethanol, which is evaporated off when the reaction is complete. This semicarbazone, preferably without being isolated beforehand, is then cyclized to give the dihalopyridazone of the formula IV by boiling in glacial acetic acid or acetic anhydride or by heating in an aqueous mineral acid, eg. hydrochloric acid, at no higher than 100° C. or by stirring in a concentrated mineral acid, eg. sulfuric acid, at room temperature (German Laid-Open Applications DOS 1,695,840, DOS 2,526,643 and DOS 1,545,595). The reaction can be carried out batchwise or continuously, and the product can be worked up by a conventional method.

The 4,5-dimethoxypyridazones of the formula I where X is oxygen or sulfur and n is 1 can be prepared by reacting a 4,5-dimethoxypyridazone of the formula

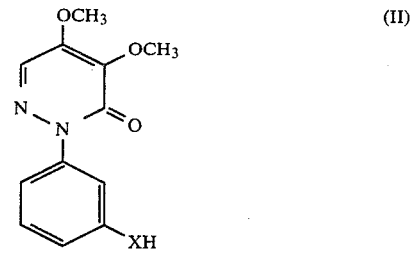

where X is oxygen or sulfur, with about the stoichiometric amount of an alkyl halide of the formula $$\text{Hal—(CR}^1\text{R}^2)_m\text{—Y}_p\text{—(CR}^1\text{R}^2)_q\text{—}\begin{array}{c}Z^1\\Z^2\\Z^3\end{array} \quad (III)$$

where $R^1$, $R^2$, Y, $Z^1$, $Z^2$, $Z^3$, m, p and q have the above meanings and Hal is halogen, in particular chlorine or bromine, in the presence of an inert organic solvent and in the presence or absence of an acid acceptor at from 0° to 150° C. The reaction can be carried out under atmospheric or superatmospheric pressure, continuously or batchwise (process b).

If 1-(3′-hydroxyphenyl)-4,5-dimethoxypyridaz-6-one and benzyl chloride are used as starting materials, the course of the reaction can be represented by the following equation:

[reaction scheme showing (II) + (III) → (I) with loss of HCl]

The starting materials are used in about stoichiometric amounts, ie. in an amount of from 0.9 to 1.1 moles of starting material III per mole of II. If necessary, an acid acceptor can be added in order to complete the reaction. Furthermore, the hydrogen halide formed during the reaction can be expelled by passing in an inert gas, such as nitrogen. The process is advantageously carried out as follows: a solution of the benzyl chloride III in an inert organic solvent is run, at 0°–30° C., if appropriate simultaneously with an equimolar amount of an acid acceptor, into a solution or suspension of the starting material II in an inert organic solvent, eg. dimethylformamide.

To complete the reaction, stirring is continued for from 0.5 to 48, preferably from 2 to 12, hours at from 30° to 150° C. The reaction mixture is worked up in a conventional manner. If the end product is obtained in solid form, it is isolated by, for example, filtering off the precipitate under suction. If, on the other hand, the end product remains dissolved in the solvent, the latter is distilled off under reduced pressure, the residue is stirred with water, and the product is then filtered off under suction. The product can be purified by, for example, recrystallization or chromatography.

Solvents which can be used for the two processes (a) and (b) are organic solvents which are inert under the particular reaction conditions. Examples of suitable solvents are halohydrocarbons, in particular chlorohydrocarbons, eg. tetrachloroethylene, 1,1,2,2- and 1,1,1,2-tetrachloroethane, dichloropropane, methylene chloride, dichlorobutane, chloroform, chloronaphthalene, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, p- and m-dichlorobenzene, o-, p- and m-dibromobenzene, o-, m- and p-chlorotoluene and 1,2,4-trichlorobenzene; ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichlorodiethyl ether; nitrohydrocarbons, such as nitromethane, nitroethane, nitrobenzene, o-, m- and p-chloronitrobenzene and o-nitrotoluene; nitriles, such as acetonitrile, butyronitrile, isobutyronitrile, benzonitrile and m-chlorobenzonitrile; aliphatic and cycloaliphatic hydrocarbons, eg. heptane, pinane, nonane, o-, m- and p-cymene, gasoline fractions boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; esters, eg. ethyl acetate, ethyl acetoacetate and isobutyl acetate; amides, eg. formamide, methylformamide and dimethylformamide, and ketones, eg. acetone and methyl ethyl ketone, as well as mixtures of these. Advantageously, the solvent is used in an amount of from 100 to 2,000, preferably from 200 to 700, % by weight, based on the starting materials.

Any conventional acid acceptor can be used for process (b). Such acid acceptors preferably include tertiary amines, alkaline earth metal compounds, ammonium compounds and alkali metal compounds, as well as mixtures of these. However, zinc compounds can also be used. Examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, tri-amylamine, diisopropylethylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethyl-pyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, -picoline, -picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurylamine and triethylenediamine.

The starting compounds are prepared by a conventional method. For example, the phenylhydrazines of the formula V are obtained from the corresponding anilines by diazotization and reduction, by a conventional method (Houben-Weyl, Methoden der organischen Chemie, volume 10/2, page 180, Georg Thieme Verlag, Stuttgart, 1967). The conversion to the corresponding pyrazone can be carried out without isolating the hydrazines, but purer products are obtained if the phenylhydrazines are isolated as hydrochlorides beforehand.

Some of the anilines are also known from the literature (German Laid-Open Application DOS 2,846,723). Those which are not known can be prepared by a conventional method.

The oxidation of thioethers to the corresponding sulfoxides or sulfones is a well known reaction and can be carried out in a conventional manner.

The Examples which follow illustrate the preparation of the compounds of the formula I. Parts by weight bear the same relation to parts by volume as that of the kilogram to the liter.

EXAMPLE 1

(a) A suspension of 49.8 parts by weight of 3-phenoxymethylaniline in 400 parts by volume of glacial acetic acid and 70 parts by volume of concentrated hydrochloric acid was reacted with a solution of 17.25 parts by weight of sodium nitrite in 45 parts by volume of water at from 10° to 20° C. A solution of 118 parts by weight of $SnCl_2.2H_2O$ in 80 parts by volume of concentrated hydrochloric acid was then added, the mixture was cooled to 0° C. and the corresponding hydrazine hydrochloride was isolated by filtering it off under suction.

(b) A suspension of 43.2 parts by weight of the hydrazine hydrochloride isolated in this manner and 33.4 parts by weight of mucochloric acid in 200 parts by volume of acetic acid was heated at the boil for 10 minutes, after which the reaction mixture was cooled, and stirred into 1,000 parts by volume of water. The precipitate was then filtered off under suction and recrystallized from ethanol. 53 parts by weight of 1-(3'-phenoxymethylphenyl)-4,5-dichloropyridaz-6-one of melting point 92°–94° C. were obtained.

(c) A suspension of 15 parts by weight of this product, 2.3 parts by weight of sodium methylate and 0.1 part by weight of N-methylpyrrolidone in 150 parts by volume of absolute toluene was stirred at 60° C. for 2 hours. The resulting solution was diluted with 200 parts by volume of ether, treated with twice 100 parts by volume of water, dried and filtered, and the filtrate was evaporated down under reduced pressure. The oily residue was triturated with diisopropyl ether, and the product was filtered off under suction. 13 parts by weight (90% of theory) of 1-(3′-phenoxymethylphenyl)-4,5-dimethoxypyridaz-6-one of melting point 82°–85° C. were obtained (compound No. 1).

The compounds of the formula I which are listed in Table 1 below can be prepared by the method described in the Example above:

TABLE

| Compound no. | X | $(CR^1R^2)_m$ | Y | $(CR^1R^2)_q$ | $Z^1$ / $Z^2$ / $Z^3$ | M.p.[°C.]/$n_D^{25}$/wavelength of a band in infrared spectrum |
|---|---|---|---|---|---|---|
| 2 | — | CH$_2$ | O | — | 4-fluorophenyl | 95–99 |
| 3 | — | CH$_2$ | O | — | 3-fluorophenyl | 108–112 |
| 4 | — | CH$_2$ | O | — | 2-fluorophenyl | |
| 5 | — | CH$_2$ | O | — | 4-chlorophenyl | 77–80 |
| 6 | — | CH$_2$ | O | — | 3-chlorophenyl | |
| 7 | — | CH$_2$ | O | — | 2-clorophenyl | |
| 8 | — | CH$_2$ | O | — | 4-bromophenyl | 1.6197 |
| 9 | — | CH$_2$ | O | — | 3-bromophenyl | |
| 10 | — | CH$_2$ | O | — | 2-bromophenyl | |
| 11 | — | CH$_2$ | O | — | 2,4-difluorophenyl | |
| 12 | — | CH$_2$ | O | — | 3,4-difluorophenyl | |
| 13 | — | CH$_2$ | O | — | 2,4-dichlorophenyl | 89–93 |
| 14 | — | CH$_2$ | O | — | 3,4-dichlorophenyl | 91–95 |
| 15 | — | CH$_2$ | O | — | 3,5-dichlorophenyl | |
| 16 | — | CH$_2$ | O | — | 2,4-dibromophenyl | |
| 17 | — | CH$_2$ | O | — | 3,4-dibromophenyl | |
| 18 | — | CH$_2$ | O | — | 2-chloro-4-fluorophenyl | |
| 19 | — | CH$_2$ | O | — | 2-bromo-4-fluorophenyl | |
| 20 | — | CH$_2$ | O | — | 2-chloro-4-bromophenyl | |
| 21 | — | CH$_2$ | O | — | 2,4,6-trichlorophenyl | |
| 22 | — | CH$_2$ | O | — | 4-nitrophenyl | |
| 23 | — | CH$_2$ | O | — | 4-cyanophenyl | |
| 24 | — | CH$_2$ | O | — | 4-methylphenyl | 83–86 |
| 25 | — | CH$_2$ | O | — | 3-methylphenyl | |
| 26 | — | CH$_2$ | O | — | 4-ethylphenyl | |
| 27 | — | CH$_2$ | O | — | 3-ethylphenyl | |
| 28 | — | CH$_2$ | O | — | 4-tert.-butylphenyl | 50–55 |
| 29 | — | CH$_2$ | O | — | 3-tert.-butylphenyl | |
| 30 | — | CH$_2$ | O | — | 2-chloro-4-methylphenyl | |
| 31 | — | CH$_2$ | O | — | 3-chloro-4-methylphenyl | |
| 32 | — | CH$_2$ | O | — | 4-trifluoromethylphenyl | |
| 33 | — | CH$_2$ | O | — | 3-trifluoromethylphenyl | 76–81 |
| 34 | — | CH$_2$ | O | — | 2-trifluoromethylphenyl | |
| 35 | — | CH$_2$ | O | — | 2-chloro-4-trifluoromethylphenyl | |
| 36 | — | CH$_2$ | O | — | 2,6-dichloro-4-trifluoromethylphenyl | |
| 37 | — | CH$_2$ | O | — | 4-methoxyphenyl | |
| 38 | — | CH$_2$ | O | — | 3-methoxyphenyl | |
| 39 | — | CH$_2$ | O | — | 4-ethoxyphenyl | |
| 40 | — | CH$_2$ | O | — | 3-ethoxyphenyl | |
| 41 | — | CH$_2$ | O | — | 2-chloro-4-methoxyphenyl | |
| 42 | — | CH$_2$ | O | — | 4-trifluoromethoxyphenyl | |
| 43 | — | CH$_2$ | O | — | 3-trifluoromethoxyphenyl | |
| 44 | — | CH$_2$ | O | — | 3-tetrafluoroethoxyphenyl | |
| 45 | — | CH$_2$ | O | — | 3-difluoromethoxyphenyl | |
| 46 | — | CH$_2$ | O | — | 4-methylmercaptophenyl | |
| 47 | — | CH$_2$ | O | — | 3-methylmercaptophenyl | |
| 48 | — | CH$_2$ | O | — | 3-trifluoromethylmercaptophenyl | |
| 49 | — | CH$_2$ | O | — | 3-methylsulfinylphenyl | |
| 50 | — | CH$_2$ | O | — | 3-methylsulfonylphenyl | |
| 51 | — | CH$_2$CH$_2$ | O | — | phenyl | |
| 52 | — | CH$_2$CH$_2$ | O | — | 4-chlorophenyl | |
| 53 | — | CH$_2$CH$_2$ | O | — | 2,4-dichlorophenyl | |
| 54 | — | CH$_2$CH$_2$ | O | — | 4-trifluoromethylphenyl | |
| 55 | — | CH$_2$CH$_2$CH$_2$ | O | — | phenyl | |
| 56 | — | CH$_2$CH$_2$CH$_2$ | O | — | 4-chlorophenyl | |
| 57 | — | CH$_2$CH$_2$CH$_2$CH$_2$ | O | — | phenyl | |
| 58 | — | CH$_2$CH$_2$CH$_2$CH$_2$ | O | — | 4-chlorophenyl | |
| 59 | — | CH(CH$_3$) | O | — | phenyl | |
| 60 | — | CH$_2$CH(CH$_3$)CH$_2$ | O | — | phenyl | |
| 61 | — | CH$_2$C(CH$_3$)$_2$ | O | — | phenyl | |
| 62 | O | CH$_2$ | — | — | phenyl | |
| 63 | O | CH$_2$ | — | — | 4-fluorophenyl | |
| 64 | O | CH$_2$ | — | — | 3-fluorophenyl | 70–72 |
| 65 | O | CH$_2$ | — | — | 2-fluorophenyl | |
| 66 | O | CH$_2$ | — | — | 4-chlorophenyl | 40–48 |
| 67 | O | CH$_2$ | — | — | 3-chlorophenyl | |
| 68 | O | CH$_2$ | — | — | 2-chlorophenyl | |

TABLE-continued

![structure: phenyl ring with Z¹, Z², Z³ substituents]

| Compound no. | X | $(CR^1R^2)_m$ | Y | $(CR^1R^2)_q$ | Z³ (aryl group) | M.p.[°C.]/$n_D^{25}$/wavelength of a band in infrared spectrum |
|---|---|---|---|---|---|---|
| 69 | O | CH$_2$ | — | — | 4-bromophenyl | |
| 70 | O | CH$_2$ | — | — | 3-bromophenyl | |
| 71 | O | CH$_2$ | — | — | 2,4-dichlorophenyl | |
| 72 | O | CH$_2$ | — | — | 2,6-dichlorophenyl | 127–131 |
| 73 | O | CH$_2$ | — | — | 4-methylphenyl | |
| 74 | O | CH$_2$ | — | — | 3-methylphenyl | |
| 75 | O | CH$_2$ | — | — | 4-ethylphenyl | |
| 76 | O | CH$_2$ | — | — | 3-ethylphenyl | |
| 77 | O | CH$_2$ | — | — | 4-trifluoromethylphenyl | 55–60 |
| 78 | O | CH$_2$ | — | — | 3-trifluoromethylphenyl | |
| 79 | O | CH$_2$ | — | — | 2-chloro-4-trifluoromethylphenyl | |
| 80 | O | CH$_2$ | — | — | 4-methoxyphenyl | |
| 81 | O | CH$_2$ | — | — | 3-methoxyphenyl | |
| 82 | O | CH$_2$ | — | — | 4-trifluoromethoxyphenyl | |
| 83 | O | CH$_2$ | — | — | 3-trifluoromethoxyphenyl | |
| 84 | O | CH$_2$ | — | — | 4-methylmercaptophenyl | |
| 85 | O | CH$_2$ | — | — | 3-methylmercaptophenyl | |
| 86 | O | CH$_2$ | — | — | 3-trifluoromethylmercaptophenyl | |
| 87 | O | CH$_2$CH$_2$ | — | — | phenyl | 80–83 |
| 88 | O | CH$_2$CH$_2$ | — | — | 4-chlorophenyl | |
| 89 | O | CH$_2$CH$_2$CH$_2$ | — | — | phenyl | 1.6023 |
| 90 | O | CH$_2$CH$_2$CH$_2$ | — | — | 4-chlorophenyl | |
| 91 | O | CH(CH$_3$) | — | — | phenyl | |
| 92 | O | CH$_2$C(CH$_3$)$_2$ | — | — | phenyl | |
| 93 | O | CH$_2$CH(CH$_3$)CH$_2$ | — | — | phenyl | |
| 94 | O | CH$_2$ | O | — | phenyl | |
| 95 | O | CH$_2$ | O | — | 4-chlorophenyl | 102–105 |
| 96 | O | CH$_2$CH$_2$ | O | — | phenyl | 94–98 |
| 97 | O | CH$_2$CH$_2$ | O | — | 4-chlorophenyl | 118–21 |
| 98 | O | CH$_2$CH$_2$CH$_2$ | O | — | phenyl | 55–60 |
| 99 | O | CH$_2$CH$_2$CH$_2$ | O | — | 4-chlorophenyl | |
| 100 | O | CH$_2$CH$_2$CH$_2$CH$_2$ | O | — | phenyl | 1.5932 |
| 101 | O | CH$_2$CH$_2$CH$_2$CH$_2$ | O | — | 4-chlorophenyl | 71–75 |
| 102 | — | CH$_2$ | O | CH$_2$ | phenyl | 1.6013 |
| 103 | — | CH$_2$ | O | CH$_2$ | 4-chlorophenyl | |
| 104 | — | CH(CH$_3$) | O | CH$_2$ | phenyl | 1.5854 |
| 105 | — | CH$_2$ | S | — | phenyl | 85–90 |
| 106 | — | CH$_2$ | S | — | 4-fluorophenyl | |
| 107 | — | CH$_2$ | S | — | 3-fluorophenyl | |
| 108 | — | CH$_2$ | S | — | 4-chlorophenyl | 70–74 |
| 109 | — | CH$_2$ | S | — | 3-chlorophenyl | |
| 110 | — | CH$_2$ | S | — | 4-bromophenyl | |
| 111 | — | CH$_2$ | S | — | 2,4-dichlorophenyl | |
| 112 | — | CH$_2$ | S | — | 2,4,6-trichlorophenyl | |
| 113 | — | CH$_2$ | S | — | 4-cyanophenyl | |
| 114 | — | CH$_2$ | S | — | 4-methylphenyl | |
| 115 | — | CH$_2$ | S | — | 3-methylphenyl | |
| 116 | — | CH$_2$ | S | — | 2-chloro-4-methylphenyl | |
| 117 | — | CH$_2$ | S | — | 4-trifluoromethylphenyl | |
| 118 | — | CH$_2$ | S | — | 3-trifluoromethylphenyl | |
| 119 | — | CH$_2$ | S | — | 2-chloro-4-trifluoromethylphenyl | |
| 120 | — | CH$_2$ | S | — | 4-methoxyphenyl | |
| 121 | — | CH$_2$ | S | — | 3-methoxyphenyl | |
| 122 | — | CH$_2$ | S | — | 3-trifluoromethoxyphenyl | |
| 123 | — | CH$_2$CH$_2$ | S | — | phenyl | |
| 124 | — | CH$_2$CH$_2$ | S | — | 4-chlorophenyl | |
| 125 | — | CH$_2$CH$_2$CH$_2$ | S | — | phenyl | |
| 126 | S | CH$_2$ | — | — | phenyl | 60–64 |
| 127 | S | CH$_2$ | — | — | 4-fluorophenyl | 70–73 |
| 128 | S | CH$_2$ | — | — | 3-fluorophenyl | 55–60 |
| 129 | S | CH$_2$ | — | — | 4-chlorophenyl | 70–74 |
| 130 | S | CH$_2$ | — | — | 3-chlorophenyl | 65–70 |
| 131 | S | CH$_2$ | — | — | 2-chlorophenyl | |
| 132 | S | CH$_2$ | — | — | 4-bromophenyl | |
| 133 | S | CH$_2$ | — | — | 3-bromophenyl | |
| 134 | S | CH$_2$ | — | — | 2,4-dichlorophenyl | |
| 135 | S | CH$_2$ | — | — | 2,6-dichlorophenyl | 82–85 |
| 136 | S | CH$_2$ | — | — | 2-cyanophenyl | 1.6371 |
| 137 | S | CH$_2$ | — | — | 4-methylphenyl | 70–75 |
| 138 | S | CH$_2$ | — | — | 3-methylphenyl | 1.6374 |
| 139 | S | CH$_2$ | — | — | 4-trifluoromethylphenyl | 50–53 |
| 140 | S | CH$_2$ | — | — | 3-trifluoromethylphenyl | |
| 141 | S | CH$_2$ | — | — | 2-chloro-4-trifluoromethylphenyl | |
| 142 | S | CH$_2$ | — | — | 4-methoxyphenyl | |
| 143 | S | CH$_2$ | — | — | 3-methoxyphenyl | |
| 144 | S | CH$_2$ | — | — | 4-trifluoromethoxyphenyl | |
| 145 | S | CH$_2$ | — | — | 3-trifluoromethoxyphenyl | |

TABLE-continued

| Compound no. | X | $(CR^1R^2)_m$ | Y | $(CR^1R^2)_q$ | ⟨phenyl with $Z^1, Z^2, Z^3$⟩ | M.p.[°C.]/$n_D^{25}$/wavelength of a band in infrared spectrum |
|---|---|---|---|---|---|---|
| 146 | S | CH$_2$CH$_2$ | — | — | phenyl | |
| 147 | S | CH$_2$CH$_2$ | — | — | 4-chlorophenyl | |
| 148 | S | CH$_2$CH$_2$CH$_2$ | — | — | phenyl | |
| 149 | S | CH$_2$CH$_2$CH$_2$ | — | — | 4-chlorophenyl | |
| 150 | S | CH$_2$CH$_2$CH$_2$CH$_2$ | — | — | phenyl | |
| 151 | S | CH$_2$CH$_2$CH$_2$CH$_2$ | — | — | 4-chlorophenyl | |
| 152 | S | CH(CH$_3$)$_2$ | — | — | 4-chlorophenyl | |
| 153 | S | CH(CH$_3$)$_2$ | — | — | phenyl | |
| 154 | S | CH$_2$CH(CH$_3$)CH$_2$ | — | — | phenyl | |
| 155 | S | CH$_2$ | O | — | phenyl | |
| 156 | S | CH$_2$ | O | — | 4-chlorophenyl | |
| 157 | S | CH$_2$CH$_2$ | O | — | phenyl | |
| 158 | S | CH$_2$CH$_2$ | O | — | 4-chlorophenyl | |
| 159 | S | CH$_2$CH$_2$CH$_2$ | O | — | phenyl | |
| 160 | S | CH$_2$CH$_2$CH$_2$ | O | — | 4-chlorophenyl | |
| 161 | S | CH$_2$CH$_2$CH$_2$CH$_2$ | O | — | phenyl | |
| 162 | S | CH$_2$ | S | — | phenyl | |
| 163 | S | CH$_2$CH$_2$ | S | — | phenyl | |
| 164 | S | CH$_2$CH$_2$CH$_2$ | S | — | phenyl | |
| 165 | O | CH$_2$ | S | — | phenyl | |
| 166 | O | CH$_2$CH$_2$ | S | — | phenyl | |
| 167 | O | CH$_2$CH$_2$CH$_2$ | S | — | phenyl | |
| 168 | — | CH$_2$ | SO | — | phenyl | |
| 169 | — | CH$_2$ | SO$_2$ | — | phenyl | |
| 170 | — | CH$_2$ | SO | — | 4-chlorophenyl | |
| 171 | — | CH$_2$ | SO$_2$ | — | 4-chlorophenyl | |
| 172 | SO | CH$_2$ | — | — | phenyl | |
| 173 | SO$_2$ | CH$_2$ | — | — | phenyl | |
| 174 | SO | CH$_2$ | — | — | 4-fluorophenyl | |
| 175 | SO$_2$ | CH$_2$ | — | — | 4-fluorophenyl | |
| 176 | SO | CH$_2$ | — | — | 3-chlorophenyl | |
| 177 | SO$_2$ | CH$_2$ | — | — | 3-chlorophenyl | |
| 178 | SO | CH$_2$ | — | — | 4-trifluoromethylphenyl | |
| 179 | SO$_2$ | CH$_2$ | — | — | phenyl | |
| 180 | — | CH$_2$ | S | CH$_2$ | phenyl | |
| 181 | — | CH$_2$ | SO | CH$_2$ | phenyl | |
| 182 | — | CH$_2$ | SO | CH$_2$ | phenyl | |

The 4,5-dimethoxypyridazones of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dipersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acid with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 3 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound no. 5 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound no. 33 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 126 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound no. 130 is intimately mixed with 95 parts by weight of particulate kaolin. A dust is obtained containing 5% by weight of the active ingredient.

VII. 30 parts by weight of compound no. 108 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 28 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well when they are applied postemergence, application techniques may be used in which the herbicidal agents are sprayed from suitable equipment in such a manner that the leaves of senstive crop plants are if possible not touched, and the agents reach the soil or the unwanted plants growing beneath the crop plants (post-directed, lay-by treatment).

The amount of active ingredient applied depends on the time of the year, the plants to be combated and their growth stage, and varies from 0.05 to 3 kg/ha and more, but is preferably from 0.1 to 1.0 kg/ha.

The herbicidal action of 4,5-dimethoxypyridazones of the formula I is demonstrated in greenhouse experiments.

The vessels employed were plastic flowerpots having a volume of 300 $cm^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown from seedlings and were transplated to the pots a few days before treatment. No covers were placed on the pots in this treatment method. The application rates for postemergence treatment were 0.25 and 0.5 kg of active ingredient per hectare.

The pots were set up in the greenhouse—species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoted nonemergence or complete destruction of at least the visible plant parts.

The plants used in the experiments were *Abutilon theophrasti*, *Amaranthus retroflexus*, *Arachis hypogaea*, *Cassia tora*, *Centaurea cyanus*, *Chenopodium album*, *Datura stramonium*, *Desmodium tortuosum*, *Euphorbia geniculata*, *Galium aparine*, *Helianthus annuus*, *Ipomoea* spp., *Lamium* spp., *Mercurialis annua*, *Polygonum persicaria*, *Sinapis alba* and *Triticum aestivum*.

In investigations into herbicidal properties, for example compounds nos. 1, 3, 28, 33, 108 and 126 had a very good action on *Sinapis alba* when applied preemergence at a rate of 3.0 kg/ha.

On postemergence application, for instance compounds nos. 5, 129, 130 and 137, applied for example at a rate of 0.25 kg/ha, had a considerable herbicidal action on a number of unwanted broadleaved plants. Compounds nos. 33 and 3 selectively combatted unwanted plants at rates of 0.25 and 0.5 kg/ha, crops such as groundnuts and wheat being only slightly damaged, if at all. Unwanted broadleaved plants in sunflowers where selectively combatted by compounds 3, 14, 33 and 126 at rates of 0.125 and 0.25 kg/ha.

In view of the many application methods possible, the 4,5-dimethoxypyridazones of the formula I may be used in a large number of crop plants for removing unwanted plant growth, especially broadleaved annual species. The following crops may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |

-continued

| Botanical name | Common name |
|---|---|
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the 4,5-dimethoxypyridazones of the formula I, or agents containing them, may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, triazinones, uracils, benzofuran derivatives, cyclohexane-1,3-dione derivatives, etc., and others.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A substituted 4,5-dimethoxypyridazone of the formula

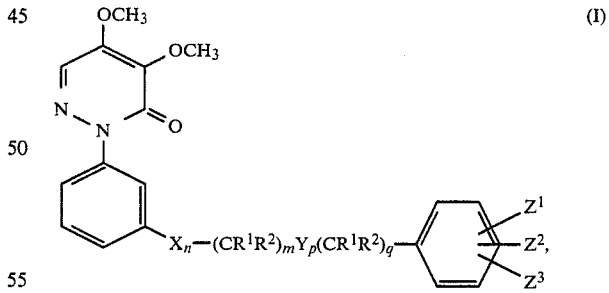

(I)

where X and Y independently of one another are each oxygen, sulfur, a sulfinyl group or a sulfonyl group, $R^1$ and $R^2$ independently of one another are each hydrogen or $C_1$–$C_4$-alkyl, $Z^1$, $Z^2$ and $Z^3$ independently of one another are each hydrogen, halogen, nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylmercapto, $C_1$–$C_4$-haloalkylmercapto, $C_1$–$C_4$-alkylsulfinyl or $C_1$–$C_4$-alkylsulfonyl, n and p are each 0 or 1, m is 1 to 8 and q is 0 to 8.

2. A substituted 4,5-dimethoxypyridazone of the formula I as defined in claim 1, where X and Y independently of one another are each oxygen or sulfur, $R^1$ and $R^2$ independently of one another are each hydrogen or $C_1$–$C_4$-alkyl, $Z^1$, $Z^2$ and $Z^3$ independently of one another are each hydrogen, halogen, $C_1$–$C_4$-alkyl, $C_1$–$C_4$-haloalkyl, $C_1$–$C_4$-alkoxy or $C_1$–$C_4$-haloalkoxy, n and p are each 0 or 1 and m is 1 and q is 0 to 8.

3. A substituted 4,5-dimethoxypyridazone of the formula I as defined in claim 1, where $R^1$ and $R^2$ are hydrogen, $Z^1$ is hydrogen, $Z^2$ and $Z^3$ are halogen, n is 0, m is 1, p is 1, and q is 0.

4. A substituted 4,5-dimethoxypyridazone of the formula I as defined in claim 1, where $R^1$ and $R^2$ are hydrogen, Y is oxygen, $Z^1$ and $Z^2$ are hydrogen, $Z^3$ is fluorine in the 3-position, n is 0, m is 1, p is 1, and q is 0.

5. A substituted 4,5-dimethoxypyridazone of the formula I as defined in claim 1, where $R^1$ and $R^2$ are hydrogen, Y is oxygen, $Z^1$ and $Z^2$ are hydrogen, $Z^3$ is trifluoromethyl in the 3-position, n is 0, m is 1, p is 1, and q is 0.

6. A herbicide containing inert additives and an effective amount of a 4,5-dimethoxypyridazone of the formula I as defined in claim 1.

7. A herbicide containing inert additives and an effective amount of a 4,5-dimethoxypyridazone of the formula I as defined in claim 2.

8. A herbicide containing inert additives and an effective amount of a 4,5-dimethoxypyridazone of the formula I as defined in claim 3.

9. A process for combatting the growth of unwanted broadleaved plants, wherein the unwanted plants or the area to be kept free from unwanted plants are treated with a herbicidally effective amount of a 4,5-dimethoxypyridazone of the formula I as defined in claim 1.

10. A process for combatting the growth of unwanted broadleaved plants as defined in claim 9, wherein the application rate is from 0.05 to 3 kg of dimethoxypyridazone per hectare.

11. A substituted 4,5-dimethoxypyridazone of the formula I as defined in claim 1, wherein m is 1.

12. A substituted 4,5-dimethoxypyridazone of the formula I as defined in claim 1, where X and Y independently of one another are each oxygen, sulfur, a sulfinyl group or a sulfonyl group, $R^1$ and $R^2$ independently of one another are each hydrogen or $C_1$–$C_4$-alkyl, $Z^1$, $Z^2$ and $Z^3$ independently of one another are each hydrogen, halogen, nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylmercapto, $C_1$–$C_4$-haloalkylmercapto, $C_1$–$C_4$-alkylsulfinyl or $C_1$–$C_4$-alkylsulfonyl, n is 0, p is 1 and q is 0.

13. A substituted 4,5-dimethoxypyridazone of the formula I as defined in claim 1, where X and Y independently of one another are each oxygen or sulfur, $R^1$ and $R^2$ independently of one another are each oxygen or sulfur, $R^1$ and $R^2$ independently of one another are hydrogen or $C_1$–$C_4$-alkyl, $Z^1$, $Z^2$ and $Z^3$ independently of one another are each hydrogen, halogen, $C_1$–$C_4$-alkyl, $C_1$–$C_4$-haloalkyl, $C_1$–$C_4$-alkoxy or $C_1$–$C_4$-haloalkoxy, n is 0, p is 1 and q is 0.

14. A substituted, 4,5-dimethoxypyridazone as defined in claim 12, wherein m is 1.

15. A substituted, 4,5-dimethoxypyridazone as defined in claim 13, wherein m is 1.

* * * * *